United States Patent [19]

Gee et al.

[11] Patent Number: 4,733,677

[45] Date of Patent: Mar. 29, 1988

[54] HAIR FIXATIVE COMPOSITION CONTAINING CATIONIC ORGANIC POLYMER AND POLYDIORGANOSILOXANE MICROEMULSIONS

[75] Inventors: Ronald P. Gee; Gretchen S. Kohl, both of Midland, Mich.

[73] Assignee: Dow Corning Corporation, Midland, Mich.

[21] Appl. No.: 926,760

[22] Filed: Nov. 4, 1986

[51] Int. Cl.[4] .............................................. A45D 7/00
[52] U.S. Cl. ........................................................ 132/7
[58] Field of Search ............................................. 132/7

[56] References Cited

U.S. PATENT DOCUMENTS

| | | | |
|---|---|---|---|
| 4,493,824 | 1/1985 | Abe | 132/7 |
| 4,586,518 | 5/1986 | Gornwall | 132/7 |
| 4,588,760 | 5/1986 | Jachowicz | 132/7 |
| 4,591,610 | 5/1986 | Grollier | 132/7 |

*Primary Examiner*—Gregory E. McNeill
*Attorney, Agent, or Firm*—Marc C. Pawl

[57] ABSTRACT

Hair fixative preparations suitable for application to hair without subsequent rinsing are disclosed. The preparations are clear, aqueous mixtures of polydiorganosiloxane and a cationic, organic polymer. The preparations are used for setting hair and may be formulated into lotion and gel type products with superior aesthetics because of the clarity of the mixtures. The preparations are effective in providing flexible, long-lasting hold for hair styles.

20 Claims, No Drawings

HAIR FIXATIVE COMPOSITION CONTAINING CATIONIC ORGANIC POLYMER AND POLYDIORGANOSILOXANE MICROEMULSIONS

BACKGROUND OF THE INVENTION

This invention relates to a composition for fixing and setting curls in hair. More particularly, the invention relates to clear mixtures of polydiorganosiloxane and cationic organic polymer components in a hair fixative formulation which is applied to hair without subsequent rinsing to provide combable and long-lasting hair styles.

Many popular hair styles require a means to hold the hair in a desired configuration. Several procedures are commonly used for setting hair styles at home and in beauty salons including, for example, the winding of wetted hair around curlers or rods followed by drying; the winding of moist hair around a hot curling iron; and the blow dring of wet hair while rolling the hair around a hand held brush. It is generally recognized that the physical and chemical action of water plays a significant role in the process of setting hair. When hair is wetted, hydrogen bonds in the keratin of hair are broken. Then when hair is shaped using curlers, iron, or brush and dried, hydrogen bonds are reformed at locations different from the previous ones and the hair style is thus set.

When hair is set by the use of water alone, the hair style gradually loses its shape through the absorption of atmospheric moisture and consequent rearrangement of the hydrogen bonds. A considerable number of hair setting compositions have been suggested to improve the durability of hair styles and especially to extend the time period that a set is retained in hair. Such compositions range from the permanent wave types which operate chemically by breaking and reforming disulfide linkages in the hair protein to preparations which provide a thin layer of film forming resin on the hair which tends to bond hair fibers together thereby maintaining a prearranged shape.

Generally, the film forming resin preparations have been composed of water or alcohol solutions of anionic polymers such as polyvinylpyrrolidone, polyvinylpyrrolidonevinylacetate copolymers, polymethacrylate resins, ethyl and butyl monoesters of polymethylvinyl ether and maleic acid, or carboxylated polyvinylacetate copolymers.

Such film forming resins have been used in several different ways. Finishing sprays, for example, are applied as a fine spray (aerosol or pump system) after the hair is styled and dry. Finishing sprays extend the life of a set by providing welds between hair fibers which maintain hold even after moisture has reduced or eliminated hold derived from hydrogen bonds.

In contrast to finishing sprays, presetting preparations are applied to hair prior to shaping and drying. After drying, the hair is manipulated further with the dry resin film already on the hair in order to form the final style. Hold provided by hair fiber welds is ineffective with presetting preparations because the postdrying manipulation generally breaks up the welds. Consequently, a presetting preparation should envelope or impregnate each individual hair fiber with a thin film of resin which, while not binding to other hair fibers, will nevertheless provide the fiber with a longer lasting memory of the imposed set.

When presetting preparations containing conventional resins are used to prolong set memory, they often make the hair objectionably stiff or sticky. In addition the resin tends to produce flaky or linty particles on the hair as the film breaks up during combing or brushing. The sticky and stiff character of the resin films also makes the coated hair difficult to comb or brush and may result in damaging or breaking hairs during such operations.

Organic cationic compounds and polymers such as stearyldimethylbenzylammonium chloride, quaternary nitrogen derivatives of cellulose ethers, and homopolymers and copolymers of dimethyldiallylammonium chloride are well known for use in hair conditioning formulations. Hair conditioners facilitate combing out hair and impart softness and suppleness to the hair. Cationic polymers are further known in the art for their substantivity which enables them to become fixed to hair and to remain on hair. Taking advantage of this substantivity, hair conditioning formulations are generally applied to wet hair which is subsequently rinsed before drying so that more uniform and thinner films of components are left on the hair. In comparison to the anionic polymers, conventional cationics generally show little effect in facilitating the setting of hair styles or providing retention of hair sets over extended periods.

It is a purpose of the present invention to provide improved presetting preparations that facilitate the setting of hair styles; prolong the set memory of hair without making the hair unnaturally stiff or sticky; and provide flexible hold for hair so that it can be combed after setting without substantial loss of set memory. It is a further purpose to provide aesthetically superior preparations which are clear and transparent instead of milky white and opaque.

Todd et al. in "Silicones Provide Real Benefits for Aerosol Cosmetics," *American Perfumer and Cosmetics,* October, 1971, describe the effect of several types of silicones including dimethyl silicones ("dimethicones" by CTFA Cosmetic Ingredient Dictionary nomenclature) used as a modifier for conventional hair fixative resins for hair spray preparations. Maeder in U.S. Pat. No. 3,257,281, June 21, 1966, describes a novel hair fixative resin for use in aerosol hair treatments. The resin contains N,N-dialkylamino substituents which provided water solubility when neutralized with an acid. Maeder further teaches that an antifoam silicone oil is combined with the resin in aerosol hair preparations.

Starch in "Silicones in Hair Care Products," *Drug and Cosmetic Industry,* June 1984, discloses that dimethicone is used in a few commercial conditioners and hair sprays, but because of its tendency to form very hydrophobic films, its use in hair care products is limited. Starch further teaches that silicones which are modified or adapted by substituting some of the methyl groups on silicon by other more hydrophilic groups such as polyoxyalkylene or aminoalkyl groups have a greater variety of applications in hair care products.

Matsunaga et al. in U.S. Pat. No. 4,369,037, Jan. 18, 1983, describe a variety of hair treatment cosmetics containing cationic keratin derivatives. Specifically, a hair conditioner formulation is illustrated which consists of 1 percent cationic keratin and 3 percent dimethyl polysiloxane in water. Matsunaga et al. show that after the conditioner is applied, the hair is rinsed in running water before drying. In contrast, for using cationic keratin in presetting hair fixative formulations, Matsunaga et al. teach a composition which consists of 1 percent cationic keratin, 10 percent ethanol, 0.5 percent of a polyoxyalkylene substituted silicone, 0.1 percent perfume, and the rest water.

Cornwall et al. in U.S. Pat. No. 4,586,518, May 6, 1986, teach a hair setting method in which aminoalkyl substituted polydiorganosiloxane is applied to the hair with or without subsequent rinsing prior to setting. It is further taught that a quaternary nitrogen containing organic conditioner such as a quaternary nitrogen derivative of a cellulose ether may be combined in equal proportions with the aminoalkyl substituted polydiorganosiloxane for use in the hair setting method.

Homan et al. in U.S. patent application Ser. No. 791,047 filed Oct. 24, 1985, which is assigned to the same assignee as the present application, teach hair fixative preparations for leave-on application to hair prior to setting. The preparations contain a blend of cationic organic polymer and carboxyalkyl substituted polydimethylsiloxane. Homan et al. report that these preparations form a flexible film on the hair which holds desired shapes during combing without formint flaky or linty particles. It is further reported that the hold lasts even under humid conditions.

Gee in European Patent Application No. 138,192, published Apr. 24, 1985, describes a method of preparing microemulsions of selected polyorganosiloxanes. Gee proposes a number of uses for the microemulsions including personal care products such as hand and face lotions, creams, shampoos, hair rinses and conditioners, shaving lotions and creams. The polydiorganosiloxanes emulsified by Gee are primarily substituted by aminoalkyl or carboxyalkyl groups to facilitate the emulsification. However, Gee also teaches that certain hydroxy terminated polydimethylsiloxanes may be emulsified if the hydroxy groups provide sufficient polarity to the molecules.

However, none of the above references seem to suggest combining cationic organic resins with microemulsions of unsubstituted polydimethylsiloxanes in a hair fixative formulation for application to hair prior to setting and without subsequent rinsing.

SUMMARY OR THE INVENTION

The present invention relates to a clear, hair fixative composition suitable for application to hair without subsequent rinsing. The composition consists essentially of (A) an aqueous microemulsion of a polydiorganosiloxane which conforms generally to the formula

QMe$_2$SiO(MeRSiO)$_y$SiMe$_2$Q wherein Me denotes the methyl radical; R independently denotes methyl, ethyl, vinyl, or phenyl radicals with the proviso that at least 90 percent of R radicals are methyl, and Q denotes hydroxy, methyl, ethyl, vinyl or phenyl; and y has an average value from 20 to 2000, and (B) a cationic, organic polymer containing amine or ammonium groups in the polymer chain or joined to the polymer chain, in a suitable aqueous carrier, wherein the weight ratio of polydiorganosiloxane to organic polymer in the composition is within the range of 1:20 to 2:1.

The present invention further relates to a method of setting hair comprising the steps of: moistening the hair with water, applying to the hair an effective amount of the composition of this invention, rolling the hair around a shaping device, and drying the hair while the hair is rolled.

DETAILED DESCRIPTION OF THE INVENTION

The hair fixative compositions of the present invention contain a combination of silicone and cationic organic polymer components. When the composition is applied to hair prior to setting, it forms a film on the hair which prolongs set memory yet leaves the hair feeling and looking naturally soft. Treated hair is also easier to comb when set with the compositions of this invention than when set with the cationic organic polymer only. The composition is especially advantageous in that it produces a flexible film on hair which allows combing the hair without losing the set memory and without forming flaky or linty particles from breakup of the film. Moreover, the film prolongs retention of hair shapes over extended periods of time even under humid conditions.

The cationic, organic polymers used in the present invention are well known materials that typically are non-flowing, solid or rubbery solid materials at room temperature. The polymers are characterized primarily as having amine or ammonium groups either in the polymer chain or in substituents joined to the polymer chain. The amine or ammonium groups provide the polymers with their cationic character which is believed to be responsible for their substantivity to hair. The polymers are generally soluble or readily dispersible in water. The cationic organic polymers are described in detail in UK Patent Application 2,114,580 and in U.S. Pat. No. 4,445,521, which are hereby incorporated by reference to further describe and provide examples of the cationic, organic polymers.

Cationic, organic polymers include, among others, quaternary ammonium derivatives of cellulose ethers; copolymers of hydroxyethylcellulose and dimethyldiallylammonium halide; copolymers of vinylpyrrolidone and dimethylaminoethylmethacrylate; terpolymers of vinylcaprolactam, vinylpyrrolidone, and dimethylaminoethylmethacrylate; quaternary ammonium derivatives of copolymers of vinylpyrrolidone and dimethylaminoethylmethacrylate; copolymers of acrylamide and dimethyldiallylammonium halide; and quaternary ammonium derivatives of copolymers of acrylamide and dimethylaminoethylmethacrylate. Although any of the cationic, organic polymers can be used in the compositions of this invention, polymers containing quaternary ammonium groups are preferred. Compositions containing these polymers provide more effective and more durable films when applied to hair.

Specific preferred polymers include quaternary ammonium derivatives of cellulose ethers, copolymers of hydroxyethylcellulose and dimethyldiallylammonium halide, quaternary ammonium derivatives of copolymers of vinylpyrrolidone and dimethylaminoethylmethacrylate, copolymers of acrylamide and dimethyldiallylammonium halide, and quaternary ammonium derivatives of copolymers of acrylamide and dimethylaminoethylmethacrylate. Among the preferred polymers, the copolymers of acrylamide and dimethyldiallylammonium halide and the copolymers of hydroxyethylcellulose and dimethyldiallylammonium halide are most preferred.

The polydiorganosiloxanes used in the present invention range from thin fluids having a viscosity of about 20 centistokes at 25° C. to thick gums having viscosities of a million centistokes or more. The diorganosiloxane polymers are generally described by the formula $$QMe_2SiO(MeRSiO)_ySiMe_2Q$$

wherein Me denotes the methyl radical; each R independently denotes methyl, ethyl, vinyl, or phenyl radicals, and Q denotes hydroxy, methyl, ethyl, vinyl, or phenyl radicals. The diorganosiloxane polymers most useful in this invention are predominately methyl substituted polymers wherein at least 90 percent of R radicals in the formula are methyl groups. It is most preferred to use polydimethylsiloxanes wherein essentially all R radicals are methyl groups. However, minor amounts, up to about 10 percent, of other hydrophobic substituents such as ethyl, vinyl, and phenyl generally do not change the character of polydimethylsiloxanes greatly and such polymers are anticipated to function equivalently in the present invention. The polymer chains may be terminated by triorganosiloxane units such as trimethylsiloxane and dimethylvinylsiloxane or by hydroxyl groups.

In the general formula for polydiorganosiloxanes, the value of y is referred to as the degree of polymerization of the polymer. This value essentially determines the viscosity of the polymer and may vary from about 20 to 2000 for the materials most useful in this invention. Generally, polydiorganosiloxane having a viscosity of about 200 to 30,000 cs at 25° C. are preferred because they are easily prepared by emulsion polymerization and because they perform advantageously with a wide range of cationic, organic resins. Polydiorganosiloxane within the preferred range of viscosities have average degrees of polymerization of from about 100 to about 750.

The polydimethylsiloxanes are known materials (referred to as "dimethicone" in the CTFA Cosmetic Ingredient Dictionary) which are commercially available in a variety of viscosities. Polydimethylsiloxanes are hydrophobic oils which are insoluble in water. Consequently, polydiorganosiloxanes must be compatibilized with water in order to form fixative preparations. More specifically for the purposes of this invention, the silicone must be compatibilized in a manner that provides clear transparent aqueous mixtures with the organic resin. While milky-white macroemulsions of silicones are well known, clear microemulsions are less common and more difficult to prepare.

Generally, clear microemulsions can be prepared by several techniques designed to provide dispersed silicone droplets having average diameters of less than 100 nm. For example, methods of making silicone microemulsions are described in U.S. Pat. Nos. 4,146,499, 4,052,331, and 3,975,294 and in European Patent Application No. 138,192. However, preferred microemulsions are made by an emulsion polymerization process wherein an initial macroemulsion of cyclic dimethylsiloxanes is added slowly with stirring to an aqueous solution of polymerization catalyst maintained at 95° C.

Anionic, cationic, or nonionic surfactants can be used to stabilize the initial macroemulsion of cyclics and subsequently, the microemulsion produced by the polymerization process. Generally, nonionic surfactants with hydrophilic-lipophilic balances (HLB) between about 10 and 20 are preferred as the primary stabilizing surfactant. Typically, more surfactant is required to form stable microemulsion than corresponding macroemulsions. For example, microemulsions usually contain about 10 to 100, preferably 25 to 50, parts by weight of surfactant for each 100 parts of silicone.

Any of the catalysts known for use in conventional macroemulsion polymerizations of dimethylsiloxane oligomers or cyclics can also be used in the above microemulsion polymerization process. For example, appropriate catalysts such as organic sulfonic acids and quaternary ammonium hydroxides are described more specifically in U.S. Pat. Nos. 2,891,920 and 3,294,725. After polymerization has progressed to the desired degree, the catalyst need only be neutralized to provide a stable microemulsion suitable for use in the present invention. The procedure for preparing microemulsions by emulsion polymerization is further described in commonly owned, copending U.S. patent application of Daniel Graiver and Osamu Tanaka, Ser. No. 809,090, filed Dec. 12, 1985.

Clear hair fixative compositions are prepared by mixing the organic resin with the silicone microemulsion. The organic resin may be dissolved in a silicone microemulsion or an aqueous solution of the resin may be mixed with the silicone microemulsion.

The combination of cationic, organic polymer and silicone microemulsion is diluted in the aqueous carrier liquid to facilitate obtaining even and effective treatment of the hair. The carrier liquid can be water only or it can be a mixture of water and a compatible organic solvent including alcohols such as ethanol and isopropanol and glycols such as propylene glycol or other solvents as well known in the hair care art.

The amount of carrier used in the compositions is not critical and can vary over a wide range. Usually, it is preferred, for ease of application, to use compositions containing from 0.1 to about 20 percent by weight of the combination of silicone and organic polymer. It is even more preferred that the composition contain 0.5 to 8 percent by weight of the combination of silicone and organic polymer.

The weight ratio of silicone to organic polymer in the compositions of the present invention is within the range of about 1:20 to 2:1 inclusive. For example, the composition may contain 10 parts silicone and 90 parts organic polymer, 50 parts silicone and 50 parts organic polymer, or 65 parts silicone and 35 parts organic polymer. It is even more preferred to use compositions wherein the proportion of silicone to organic polymer is in the range of 1:10 to 1:1 inclusive. Compositions with the above ratio of components are preferred because they generally provide a very desirable combination of flexible fixation and conditioning effects on hair.

The compositions of this invention provide many improvements in hair characteristics that are not obtained by the use of either silicone or organic polymer alone. For example, on wet hair, the composition improves the ease of wet combing and provides a silkier touch. Once the treatment is dried, a film is formed on individual hair strands which mechanically holds the shape of the hair, but the hair continues to exhibit silkier touch and easy combing characteristics. While the organic polymer alone may provide some silkiness and improved combing, the combination with polydiorganosiloxane enhances these properties. Typically, the organic polymer alone has a tacky feel which is detackified upon addition of the silicone. Similarly, while the organic polymer alone on hair may provide some set memory effect, the combination of silicone and organic polymer on hair provides better set memory because the set is more durable, longer lasting, flexible, and lubricated for improved combing ease. The compositions of this invention containing nonpolar silicones also have the added advantage that the silicone is not substantive to hair and consequently will not build up on the hair even with frequent use.

The compositions of this invention may also contain other components such as thickeners, perfumes, colorants, preservatives, propellant gases and small amounts of acids or bases to adjust pH as desired. When the composition is intended to be applied to the hair by first placing a portion in the hand and then transferring to the hair, it is preferred that the composition contain a thickener. The concentration of thickeners when used is generally from 0.5 to 30 percent, and preferably from 0.5 to 15 percent by weight.

Thickeners which can be used include sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose and starch amylose and locust bean gum.

Perfumes which can be used in the compositions are the cosmetically acceptable perfumes and they may be present in amounts which vary from 0.1 to 0.5 percent by weight.

The present invention further relates to a method of setting hair comprising the steps of: moistening the hair with water, applying to the hair an effective amount of the composition of this invention, rolling the hair around a shaping device, and drying the hair while the hair is rolled. The steps of the method of this invention may be performed in any order or simultaneously with the only exception being that the hair is dried while the hair is rolled and, of course, after the hair has been moistened with water and treated with the fixative composition of this invention.

In the method of this invention, a desired shape or configuration is imposed on the hair by rolling the hair around a shaping device. Any of the conventional devices commonly used for setting hair styles may be employed in the method of this invention. For example the hair may be rolled on curlers, a curling iron or a hand held brush. The hair may be rolled while wet such as after shampooing or it may be rolled while dry and then moistened with water. Moistening the dry roller hair may also be accomplished simultaneously with the application of the treatment composition since the hair fixative composition is delivered in an aqueous carrier.

In the method of this invention, the composition may be applied to the surface of the hair in any suitable manner such as by massaging the composition throughout the hair by hand, by dipping the hair into the composition, by brushing or combing the composition through the hair, or by padding the hair with sponges or cloth containing absorbed treating composition. The composition may be applied either before the hair is rolled or after it is rolled. Generally, however, it is preferred to apply the composition prior to rolling the hair since it is easier to treat the hair evenly at this stage.

The hair fixative composition is formulated so that it is suitable to be applied to the hair without subsequent water rinsing. Such leave-on compositions of this invention are preferred because they provide longer-lasting shape holding properties to hair.

Generally the amount of composition is applied that is effective to provide an improvement in curl retention. The amount required will vary with the quantity and type of hair of each individual. Also the amount applied will vary depending on the extent of curl retention desired. Appropriate amounts for any individual's hair are readily determined by one or two trial applications.

The hair is dried while it is rolled in the desired shape or configuration. The hair may be dried by any convenient method such as by heating the hair with a blow dryer, with hot curlers, or with a heated curling iron. The hair may also be allowed to dry naturally at room temperature.

The following examples are presented to illustrate the invention to those skilled in the art and should not be construed as limiting the invention, which is properly delineated in the appended claims. All proportions by parts or percents are by weight unless otherwise state.

Example

This example shows the percent curl retention for hair set with preparations of this invention compared to hair set with preparations containing organic resins or silicone only.

Clear, hair fixative compositions were prepared by mixing appropriate portions of the following components in water to provide preparations containing 3% of combined silicone and organic resin solids.

Organic Results

1. CELQUAT L200, available from National Starch & Chemical Corporation, Bridgewater, NJ, is a copolymer of hydroxyethylcellulose and dimethyldiallylammonium chloride.

2. GAFQUAT 755N, available from GAF Corporation, Wayne, NJ, is a copolymer of vinylpyrrolidone and dimethylaminoethylmethacrylate which has been reacted with dimethylsulfate to form quaternary ammonium groups.

3. UCARE Polymer JR-400, available from Union Carbide Corp., Danbury, CT, is a polymeric quaternary ammonium salt of hydroxyethylcellulose reacted with a trimethylammonium substituted epoxide.

4. MERQUAT S, available from Merck & Company, Inc, Rahway, NJ, is an 8% solids aqueous solution of a resinous copolymer of acrylamide and dimethyldiallylammonium chloride.

B 5. GAFFIX VC-713, available from GAF Corporation, Wayne, NJ, is a 37% solids solution in ethanol of a copolymer of vinylcaprolactam, vinylpyrrolidone and dimethylaminoethylmethacrylate.

Silicone Microemulsions

1. Silicone Emulsion I is a transparent, anionic microemulsion having an average silicone droplet size of 25 nm diameter. The emulsion was prepared by emulsion polymerization of dimethylsiloxane cyclics and contained 18% hydroxy terminated polydimethylsiloxane having a number average molecular weight of about 22,000 and about 2% of unpolymerized dimethylsiloxane cyclics. The emulsion was stabilized by 7.7% triethanolamine dodecylbenzenesulfonate, an anionic surfactant, and 5.6% of polyoxyethylene (40) octylphenyl ether, a nonionic sufactant.

2. Silicone Emulsion II is a transparent, cationic microemulsion having an average silicon droplet size of 28 nm diameter. The emulsion was prepared by emulsion polymerization of dimethylsiloxane cyclics and contained 18% hydroxy terminated polydimethylsiloxane having a number average molecular weight of about 9,700 and about 2% of unpolymerized dimethylsiloxane cyclics. The emulsion was stabilized by 4.0% tallowtrimethylammonium chloride, a cationic surfactant, and 5.6% of polyoxyethylene (16) octylphenyl ether, a nonionic surfactant. Silicone Emulsions I and II also contained a preservative (0.00045% 5-chloro-2-methyl-4-isothiazolin-3-one) and a rust inhibitor (0.1% sodium benzoate).

Dark brown European hair tresses were prepared in two gram bundles with a length of five inches. Hair tresses were treated by massaging 0.5 cc of the hair fixative composition into the hair for 30 seconds and then combing three times. Next, each tress was individually rolled onto a ¾ inch O.D. curler and allowed to dry 12 to 14 hours at low humidity (<30% RH). Tresses were removed from the curlers, combed three times, and then hung in front of a calibrated board in a humidity chamber at 70% RH. The tress length was measured immediately after placement in the humidity chamber and again 4, 8, and 24 hours later. Percent curl retention was calculated as:

$$\% \text{ Curl Retention} = \frac{L - L_t}{L - L_o} \times 100$$

where L is the hair tress length (12.4 cm), $L_o$ is the initial tress length after removal from the curler, and $L_t$ is the tress length after time (t).

Six matching tresses were treated with each hair fixative preparation. The average percent curl retention determined for each treatment is shown in Table 1. A higher percent curl retention indicates improved set memory.

TABLE 1

| Hair Fixative Composition | | Percent Curl Retention | | |
|---|---|---|---|---|
| Cationic Resin | Silicone Emulsion | 4 hr | 8 hr | 24 hr |
| CELQUAT | None | 86.6 | 81.2 | 75.9 |
| CELQUAT | Anionic | 90.3 | 85 | 79.9 |
| CELQUAT | Cationic | 93.3 | 88.5 | 82.2 |
| GAFQUAT | None | 91 | 86 | 75.4 |
| GAFQUAT | Anionic | 96.7 | 93.2 | 82.2 |
| GAFQUAT | Cationic | 94.6 | 90.6 | 82.5 |
| UCARE | None | 92 | 87.6 | 82 |
| UCARE | Anionic | 96 | 94.3 | 91.4 |
| UCARE | Cationic | 96.5 | 92.8 | 85.9 |
| MERQUAT | None | 83.6 | 79.1 | 68.6 |
| MERQUAT | Anionic | 90.2 | 83.2 | 75.3 |
| MERQUAT | Cationic | 86.8 | 81 | 72.5 |
| GAFFIX | None | 77.3 | 76.5 | 62.8 |
| GAFFIX | Anionic | 77.7 | 69.9 | 61.9 |
| GAFFIX | Cationic | 81.8 | 74.4 | 61.3 |
| None | Anionic | 55.9 | 51.3 | 46.2 |
| None | Cationic | 77.4 | 75.9 | 65.8 |

The data shows that the preparations containing both organic resin and a silicone microemulsion generally improved curl retention under conditions of high humidity. It was also observed that dry hair released more easily from the curlers after treatments with mixtures of silicone and organic resin than when treated with only the organic resin. Additionally, hair treated with compositions of this invention was easier to comb and had better aesthetics in regard to appearance and feel.

That which is claimed is:

1. A clear, hair fixative composition suitable for application to hair without subsequent rinsing which composition consists essentially of
   (A) an aqueous microemulsion of a polydiorganosiloxane which conforms generally to the formula QMe₂SiO(MeRSiO)ySiMe₂Q wherein Me denotes a methyl radical; R independently denotes methyl, ethyl, vinyl, or phenyl radicals with the proviso that at least 90 percent of R radicals are methyl, and Q denotes hydroxy, methyl, ethyl, vinyl, or phenyl; and y has an average value from 20 to 2000, wherein the polydiorganosiloxane droplet size of said microemulsion is less than 100 nm in diameter, and
   (B) a water-soluble, cationic, organic polymer containing amine or ammonium groups in the polymer chain or joined to the polymer chain,
in a suitable aqueous carrier, wherein the weight ratio of polydiorganosiloxane to organic polymer in the composition is within the range of 1:20 to 2:1.

2. The composition of claim 1 wherein the cationic, organic polymer is selected from the group consisting of quaternary ammonium derivatives of cellulose ethers; copolymers of hydroxyethylcellulose and dimethyldiallylammonium halide; copolymers of vinylpyrrolidone and dimethylaminoethylmethacrylate; terpolymers of vinylcaprolactam, vinylpyrrolidone, and dimethylaminoethylmethacrylate; quaternary ammonium derivatives of copolymers of vinylpyrrolidone and dimethylaminoethylmethacrylate; copolymers of acrylamide and dimethyldiallylammonium halide; and quaternary ammonium derivatives of copolymers of acrylamide and dimethylaminoethylmethacrylate.

3. The composition of claim 2 wherein the cationic, organic polymer contains quaternary ammonium groups.

4. The composition of claim 3 wherein the cationic, organic polymer is selected from the group consisting of quaternary ammonium derivatives of cellulose ethers, copolymers of hydroxyethylcellulose and dimethyldiallylammonium halide, quaternary ammonium derivatives of copolymers of vinylpyrrolidone and dimethylaminoethylmethacrylate, copolymers or acrylamide and dimethyldiallylammonium halide, and quaternary ammonium derivatives of copolymers of acrylamide and dimethylaminoethylmethacrylate.

5. The composition of claim 4 wherein y has an average value of 100 to 750.

6. The composition of claim 5 wherein the ratio of polydiorganosiloxane to organic polymer in the composition is within the range of 1:10 to 1:1.

7. The composition of claim 6 wherein the composition contains 0.1 to 20 percent by weight of the combination of polydiorganosiloxane and organic polymer.

8. The composition of claim 7 wherein the carrier comprises water and the polydiorganosiloxane is dispersed in the water with a surfactant selected from the group consisting of anionic, cationic, and nonionic surfactants.

9. The composition of claim 8 wherein the composition contains 0.5 to 8 percent by weight of the combination of polydiorganosiloxane and organic polymer.

10. The composition as claimed in claim 1, wherein said microemulsion of said polydiorganosiloxane is obtained by an emulsion polymerization process wherein an initial macroemulsion of cyclic dimethylsiloxanes is combined with an aqueous solution of a polymerization catalyst by stirring.

11. A method of setting hair comprising the steps of: moistening the hair with water, applying to the hair an effective amount of a composition consisting essentially of (A) an aqueous microemulsion of a polydiorganosiloxane which conforms generally to the formula $$QMe_2SiO(MeRSiO)_ySiMe_2Q$$

wherein Me denotes a methyl radical; R independently denotes methyl, ethyl, vinyl, or phenyl radicals with the proviso that at least 90 percent of R radicals are methyl, and Q denotes hydroxy, methyl, ethyl, vinyl, or phenyl; and y has an average value from 20 to 2000, wherein the polydiorganosiloxane droplet size of said microemulsion is less than 100 nm in diameter, and (B) a water-soluble, cationic, organic polymer containing amine or ammonium groups in the polymer chain or joined to the polymer chain, in a suitable aqueous carrier, wherein the weight ratio of polydiorganosiloxane to organic polymer in the composition is within the range of 1:20 to 2:1, rolling the hair around a shaping device, and drying the hair while the hair is rolled.

12. The method of claim 11 wherein the cationic, organic polymer is selected from the group consisting of quaternary ammonium derivatives of cellulose ethers; copolymers of vinylpyrrolidone and dimethylaminoethylmethacrylate; terpolymers of vinylcaprolactam, vinylpyrrolidone, and dimethylaminoethylmethacrylate; quaternary ammonium derivatives of copolymers of vinylpyrrolidone and dimethylaminoethylmethacrylate; copolymers of acrylamide and dimethyldiallylammonium halide; and quaternary ammonium derivatives of copolymers of acrylamide and dimethylaminoethylmethacrylate.

13. The method of claim 12 wherein the cationic, organic polymer contains quaternary ammonium groups.

14. The method of claim 13 wherein the cationic, organic polymer is selected from the group consisting of quaternary ammonium derivatives of cellulose esters, quaternary ammonium derivatives of copolymers of vinylpyrrolidone and dimethylaminoethylmethacrylate, copolymers of acrylamide and dimethyldiallylammonium halide, and quaternary ammonium derivatives of copolymers of acrylamide and dimethylaminoethylmethacrylate.

15. The method of claim 14 wherein y has an average value of 100 to 750.

16. The method of claim 15 wherein the ratio of polydiorganosiloxane to organic polymer in the composition is within the range of 1:10 to 1:1.

17. The method of claim 16 wherein the composition contains 0.1 to 20 percent by weight of the combination of polydiorganosiloxane and organic polymer.

18. The method of claim 17 wherein the carrier comprises water and the polydiorganosiloxane is dispersed in the water with a surfactant selected from the group consisting of anionic, cationic, and nonionic surfactants.

19. The method of claim 18 wherein the composition contains 0.5 to 8 percent by weight of the combination of polydiorganosiloxane and organic polymer.

20. The method of claimed in claim 11, wherein said microemulsion of said polydiorganosiloxane is obtained by an emulsion polymerization process wherein an initial macroemulsion of cyclic dimethylsiloxanes is combined with an aqueous solution of a polymerization catalyst by stirring.

* * * * *